United States Patent [19]
Trooskin

[11] Patent Number: 5,647,855
[45] Date of Patent: Jul. 15, 1997

[54] SELF-HEALING DIAPHRAGM IN A SUBCUTANEOUS INFUSION PORT

[76] Inventor: Stanley Z. Trooskin, 1565 Kearney Dr., No. Brunswick, N.J. 08902

[21] Appl. No.: 267,081

[22] Filed: Jul. 5, 1994

Related U.S. Application Data

[63] Continuation of Ser. No. 879,758, May 6, 1992, abandoned.

[51] Int. Cl.$^6$ ................................................ A61M 5/32
[52] U.S. Cl. ................................... 604/175; 604/174
[58] Field of Search .................................. 604/175, 174, 604/8, 9, 28, 29, 49, 51, 86, 88, 93, 131, 187, 891.1, 415, 265; 128/764

[56] References Cited

U.S. PATENT DOCUMENTS

| | | | |
|---|---|---|---|
| 4,414,857 | 11/1983 | Brazhnikov et al. | 73/863.11 |
| 4,464,178 | 8/1984 | Dalton | 604/174 |
| 4,490,137 | 12/1984 | Moukheibir | 604/28 |
| 4,710,167 | 12/1987 | Lazorthes | 604/93 |
| 4,784,646 | 11/1988 | Feingold | 604/175 |
| 4,802,885 | 2/1989 | Weeks et al. | 604/93 |
| 4,857,053 | 8/1989 | Dalton | 604/93 |
| 5,013,298 | 5/1991 | Moden et al | 604/93 |
| 5,026,344 | 6/1991 | Dijkstra et al. | 604/93 |
| 5,045,060 | 9/1991 | Melsky et al. | 604/93 |
| 5,090,954 | 2/1992 | Geary | 604/29 |
| 5,185,003 | 2/1993 | Brethauer | 604/93 |

FOREIGN PATENT DOCUMENTS 3618390  11/1987  Germany .................. 604/187

*Primary Examiner*—Michael Powell Buiz
*Assistant Examiner*—V. Alexander
*Attorney, Agent, or Firm*—Morgan & Finnegan, L.L.P.

[57] ABSTRACT

A subcutaneous infusion port comprising a three-piece removable unit including a self-sealing, needle penetrable diaphragm having a composite membrane comprising a bottom layer that has the properties of being inert, being impermeable to fluid and preventing tissue in-growth and a middle layer laminated to the bottom layer that has the properties of promoting tissue in-growth into the middle layer.

9 Claims, 2 Drawing Sheets

SELF-HEALING DIAPHRAGM IN A SUBCUTANEOUS INFUSION PORT

This is a continuation of application Ser. No. 07/879,758 filed on May 6, 1992 now abandoned.

FIELD OF THE INVENTION

The present invention relates to a subcutaneous infusion port comprising a three-piece removable unit including a diaphragm that is both self-sealing, self-healing and leak resistant.

BACKGROUND OF THE INVENTION

The peritoneum is the largest serous membrane in the body. The part which lines the abdominal wall is named the parietal peritoneum; that which is reflected over the contained viscera constitutes the visceral peritoneum. The space between the parietal and visceral layers of the peritoneum is named the peritoneal cavity; but under normal conditions, this cavity is merely a potential one, since the parietal and visceral layers are in contact.

It is well-known that the peritoneal membrane will function effectively as an ion exchange membrane for various purposes. As early as 1923, peritoneal dialysis (an artificial kidney format) was first applied clinically. The first peritoneal access device was a piece of rubber tubing temporarily sutured in place. As early as 1960, peritoneal dialysis was becoming an established form of artificial kidney therapy for acute renal failure and, in order to lessen the discomfort of repeated, temporary punctures into the peritoneal cavity, acute or temporary peritoneal catheters were developed.

Conventionally, a peritoneal dialysis system involves introducing dialyzing fluids into the peritoneal cavity of the body by way of a catheter secured with a perforated end within the peritoneal cavity and the other end projecting through the epidermis. The dialyzing fluids is introduced into the body by opening the external end of the catheter and passing a dialyzing fluid through the catheter into the cavity for a specified time period and in quantities sufficient to permit endogenous wastes from the blood to diffuse across the peritoneal membrane using dialysis fluid to create a concentration gradient. The dialyzing fluid is then removed by siphon or a gravity technique and the procedure is repeated. This system is used to perform for both acute and chronic dialysis.

Presently, the standard methods of accomplishing peritoneal dialysis in patients with end stage renal disease are continuous ambulatory peritoneal dialysis ("CAPD") and continuous cyclic peritoneal dialysis ("CCPD"). CAPD is performed during the day, with a patient or his designee controlling both the inflow and drainage of the dialysis fluid. Typically, CAPD is done everyday and the in-flow and drainage is conducted four times with an average dwell time of approximately ½ to 2 hours for each cycle. In contrast, CCPD is performed by a machine connected to a patient, during the night while a patient sleeps, with a machine controlling the in-flow and drainage of the dialysis fluid. See, e.g., *Report of National CAPD Registry of National Institute of Health*, Lindblad et al., (1987).

In the conventional methods, the external end of the catheter exits through the epidermis where it is closed until required. This arrangement is frequently uncomfortable to a patient because the catheter projects permanently from the patient's body at some point in the abdominal wall. In addition, this system poses a serious infection problem. The open end of the catheter provides a permanent entrance for possible infection. Currently, the rate of peritonitis is 1.4 episodes per patient years. Peritonitis is an inflammation of the lining of the peritoneal cavity. It is believed that peritonitis may also be caused by microorganisms passing down the outer wall of the catheter, i.e. catheter tract, and through the biological barriers before these biological barriers have been fully integrated with the surrounding tissue.

In addition, the rate of exit site infections are 0.5 episodes per patient year for this conventional method. In an attempt to reduce infection, the patient must take a great deal of care in making sure the catheter is closed at all times when not in use and the area near the exit site of the catheter is always clean. Even with these precautions, microorganisms can enter the catheter. The patient, must be especially careful when taking a shower or swimming due to the increased risk of introducing infection through the catheter.

Moreover, in the conventional method, since the portion of the catheter exiting from the patient's body is normally held against the body with a bandage over a long period of time, there is always a potential source of localized skin problems caused by the adhesive bandage securing the catheter end. Furthermore, this exiting catheter also creates cosmetic and psychological problems for the patient. These psychological problems are particularly acute in patient with kidney problems that require many hours of dialysis every week for indefinite periods of time.

Recently, in an attempt to reduce infections and cosmetic problems associated with transepithelial catheters, injection ports have been developed which can be implanted in the body. Typically, these injection ports are used to administer medication to a patient by means of conventional hypodermic syringe.

Known injection devices of this general type have an injection chamber formed within a housing of cup-like configuration with a top end closed by a needle-penetrable, diaphragm. The diaphragm is typically located axially within a cylindrical channel formed near the open end of the housing. With this arrangement, the exposed surface of the diaphragm is generally recessed within the housing. The chamber conventionally is situated immediately below the diaphragm for receiving the medication. Typically, the medication is delivered to a desired site within the patient by means of catheter connected to a hollow stem leading from the chamber.

However, these conventional injection ports have the major disadvantage of not being capable of withstanding repeated puncturing by a needle. Moreover, since these injection ports are typically designed for administering medication, they are not suitable for applications requiring large flow rates such as peritoneal dialysis.

For example, a transcutaneous device as shown in U.S. Pat. No. 4,490,137, discloses a rigid metallic reservoir. The unyielding structure of the metallic reservoir can cause discomfort upon implantation. The device also includes a needle penetrable surface that is not self sealing. Consequently, upon withdrawal of the needle, a fluid path can be established causing leakage. There is also a possibility of reflux back along the surface of the needle during injection. Thus, this device would be totally unacceptable for any application requiring repeat usage.

In another example, subcutaneous injection sites disclosed in U.S. Pat. Nos. 4,543,088 and 5,045,060 include a needle penetrable diaphragm made of an elastic material of silicone rubber. The patents describe the sealing mechanism of the diaphragm as being established by wedging the diaphragm into the unit to provide elastic restoring forces of the silicone rubber within the diaphragm. However, with repeated punctures by large bore needles, the diaphragm loses its ability to seal which results in leakage. Moreover, due to the requirement of maintaining the diaphragm in a compressive state, the maximum size of the diaphragm is limited, and, thus, the unit would not be feasible for applications requiring large needles such as peritoneal dialysis.

In a further example, the implantable resealable puncture housing disclosed in U.S. Pat. No. 4,190,040 utilizes a laminated structure wherein a silicone gel is sandwiched between two silicone layers. Such a device did provide for a more varied angle of penetration for a hypodermic needle being inserted into the chamber. However, the housing is unacceptable for repeated puncturing with large bore hypodermic needles because gel bleeding can occur. In addition, such a device after repeated puncturing does not provide for effective sealing, particularly when the fluid in the chamber within the housing is under elevated pressures such as pressures at or near the blood pressure levels of a patient.

SUMMARY OF THE INVENTION

1. Objects of the Invention

An object of the present invention is to provide a subcutaneous infusion port comprising a diaphragm that is self-healing and thus, maintains its sealing capacity for a long duration of time.

Another object of the present invention is to provide a subcutaneous infusion port that can be connected to a standard dialysis catheter.

A further object of this invention is to provide an improved infusion port for injecting fluids into the peritoneal cavity.

Another object of the present invention is to provide an access device for peritoneal dialysis for both CAPD and CCPD in which the likelihood of biological infection is significantly reduced by eliminating the chronic catheter tract and restoring the epithelial barrier.

A further object of the present invention is to provide a peritoneal dialysis access device which does not subject the patient to physical limitations, which is comfortable for the patient and which is not likely to cause trauma.

A further object of the present invention is to provide a self-sealing diaphragm of a subcutaneous infusion port which can be used in situations requiring repeated and periodic puncturing while maintaining a self-sealing capability even under high flow rates required for both CAPD and CCPD.

An additional object of the present invention is to provide a subcutaneous injection port that includes a needle step member that substantially surrounds all access points of a needle thereby minimizing the likelihood that the needle will pass into and out of the fill chamber of the septum.

Another advantage of the present invention is to provide a three-piece arrangement that allows for the diaphragm to be replaced by minor surgery.

A further object of the present invention is to provide a subcutaneous infusion port with a large surface area diaphragm for peritoneal dialysis that does not leak while being subjected to repeat and periodic puncturing by large bore needles with either a beveled closed cutting edge or a tapered tip with side holes.

2. Brief Description of the Invention

The present invention relates to a subcutaneous infusion port comprising (1) a replaceable diaphragm consisting of a composite membrane that is both self-sealing and leak resistant; (2) a three piece unit for ease of part replacement; and (3) a conduit that connects to a standard catheter.

In one aspect of the invention, a subcutaneous infusion port, comprising:

(a) a housing forming an inner chamber and including
  (i) a vertically extending side wall disposed about the chamber, the side wall having a first and second axially spaced ends, the side wall extends in a circle, forming a generally cylindrical chamber;
  (ii) an entry port into the chamber located at the second end of the side wall;
  (iii) a bottom solid wall axially disposed at the first end of the sidewall;
  (iv) an attaching means disposed on the housing for fixing the housing to a patient;

(b) a self-sealing, needle penetrable diaphragm axially located near the second end of the sidewall for sealing the entry port and for maintaining a sealed chamber;

(c) a removable sealing means in contact with both the side wall and the diaphragm in order to securely hold the diaphragm to the housing and to provide a leak resistant seal between the diaphragm and housing;

(d) a conduit which extends through the side wall and interconnects with the inner chamber for a fluid flow passage.

In another aspect of the invention, a subcutaneous infusion port, comprising a diaphragm with a composite membrane comprising:

(a) a bottom layer constructed of a material having properties of being inert, being impermeable to fluid and preventing tissue in-growth;

(b) a middle layer laminated to the bottom, the middle layer constructed of a material having properties that promote tissue in-growth into the middle layer.

DETAILED DESCRIPTION OF THE INVENTION

Figure 1:
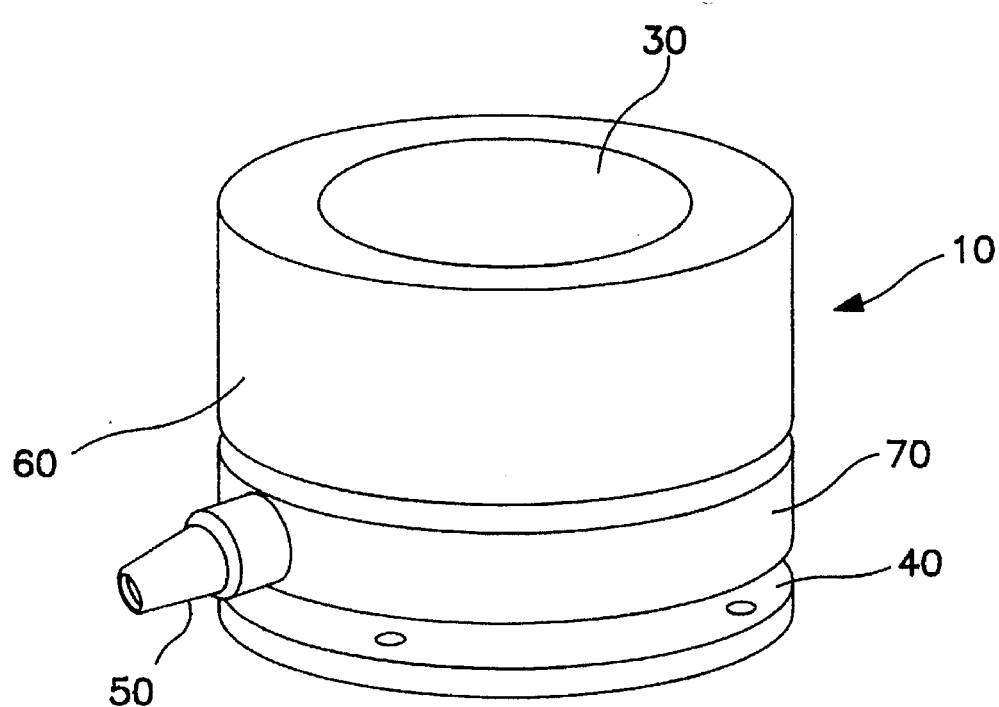
FIG. 1 is a perspective view of the subcutaneous infusion port of the present invention.

Briefly, as shown in FIG. 1, an implantable, subcutaneous infusion port in accordance with the present invention has a housing forming an inner chamber and an entry port into the chamber located at a top of the housing, a self-sealing, penetrable diaphragm axially disposed on a ledge, shoulder or edge of the top portion of the housing for closing the entry port, and a conduit which extends through a side wall of the housing and interconnects with the inner chamber for providing fluid flow passage into and out of the inner chamber. The conduit can provide for interconnecting with a standard catheter or other suitable tubing.

In a preferred embodiment, the connection at the conduit is designed to accommodate all standard commercial peritoneal catheters such as single and double cuff, straight, spiral, and disc.

In an embodiment, the self-sealing subcutaneous infusion port of the present invention includes a housing and a sealing means, which is composed of a material that is biocompatible. Suitable material includes polyethylene, polycarbonate, polyurethane, polyvinyl chloride, and metals such as stainless steel, and titanium. In addition, the housing and/or sealing means may be composed of a composite of one or more materials. In preferred embodiments, a bottom wall is composed of a material that prevents the insertion of a hypodermic needle completely through the housing when fluid is introduced into the subcutaneous infusion port. In another embodiment, the subcutaneous infusion port comprises a generally cup-shaped needle stop member having a base with a spherical contour.

In a preferred embodiment, the present invention can be subcutaneously implanted for either accomplishing CAPD and CCPD. In another embodiment, the present invention can be subcutaneously implanted for delivery of an infusate, although in some instances they are used for removal of a body fluid, e.g., blood. For example, such devices can provide for controlled drug delivery to a selected infusion site in a human or animal body for any of a variety of therapeutic purposes.

The design of the present invention provides for repeated puncture by a needle tip while introducing fluid into the inner chamber, but which retains such fluid and greatly inhibits leaking of such fluid into the surrounding tissue. In another embodiment, the present invention can be used for infusing fluids into pressurized areas which may be experienced in the body such as in the circulatory system.

Specifically, for peritoneal dialysis, large bore needles are necessary for high flow rates and low resistance across the needle. A typical size of a large bore needle for peritoneal dialysis is in the range of approximately 18 to 12 gauge.

The diaphragm of the present invention comprises a novel three layer composite membrane. In a preferred embodiment, the bottom layer forms part of the inner chamber of the housing. The bottom layer is constructed of a material that has the properties of being inert, being impermeable to fluid and preventing tissue in-growth. Such a bottom layer includes a lower layer of polytetrafluoroethylene ("PTFE") and expanded porous PTFE and an upper layer of an elastomer glue. Manufacturers of expanded porous PTFE include W. L. Gore & Associates, Inc. In another embodiment, the bottom layer may be constructed of a composite layer of materials having the desired properties. In a preferred embodiment for peritoneal dialysis, the thickness of the bottom layer is approximately 1 mm.

The middle layer of the diaphragm is constructed of a material that promotes tissue in-growth, i.e. collagen fibers from inflammatory reaction will produce tissue that will grow into the middle layer. Such materials include dacron, nylon, cotton, polyethylene or polypropylene. In another embodiment, the structure of the material is selected such that the cross-section of the material has "scaffolding," i.e. a structure to allow fibrous tissue in-growth. One method of establishing this "scaffolding" is to decrease the density of the material by employing a mesh, lattice work or fluffing the material with, for example, a sharp object. In another embodiment, the bottom layer may be constructed of a composite layer of materials having the desired properties. In a preferred embodiment for peritoneal dialysis, the thickness of the middle layer is in the range of approximately 1–10 mm. The top layer is the biological layer that involves tissue in-growth with the middle layer to create a fibrous tissue diaphragm. Since the top layer involves tissue incorporation, puncturing the diaphragm, will stimulate fibrosis which, in turn, will allow the diaphragm to get thicker with time.

The middle layer is laminated to the bottom layer by conventional methods of fastening including the application of a thin layer of silicone elastomer glue. The fastening method chosen should have the ability to permanently hold the bottom and middle layers together even under high pressures while not interfering with the material properties of the bottom layer.

In another embodiment, additional layers may be employed for additional structure, impermeability to fluid, high pressure and/or promoting tissue in-growth.

In a preferred embodiment, the subcutaneous infusion port of the present invention is secured subcutaneously in a pocket just outside the fascia. A standard dialysis catheter is connected to the conduit and its distill tip with multiple perforation is placed within the peritoneal cavity in a standard manner. After the surgical incision has healed, the patient, when not being dialyzed, has an intact epithelial barrier. When it is necessary to dialyze the patient, the diaphragm is manually located, the area over it antiseptically prepared and a needle penetrates through the epidermis until its pointed end punctures and passes through the diaphragm. Dialyzing fluid is then introduced through the needle into the diaphragm and is pushed through the conduit, into the catheter and into the peritoneal cavity. After an appropriate quantity of fluid is introduced, standard CAPD or CCPD may be accomplished. After completion of peritoneal dialysis, the needle is withdrawn, the wound cleaned and a small bandage placed over it. Since these wounds stimulate fibrosis, tissue in-growth will occur on the top layer of the diaphragm, which may result over time, in an increasing thickness of the overall diaphragm. Thus, repeated dialysis can be conducted in the same general area without ill effect.

In another embodiment, a plurality of infusion ports of the present invention can be implanted in a patient. This allows for periodic rotation of access sites to allow additional time for each access site to further heal and for additional tissue ingrowth to occur into the diaphragm.

Figure 2:
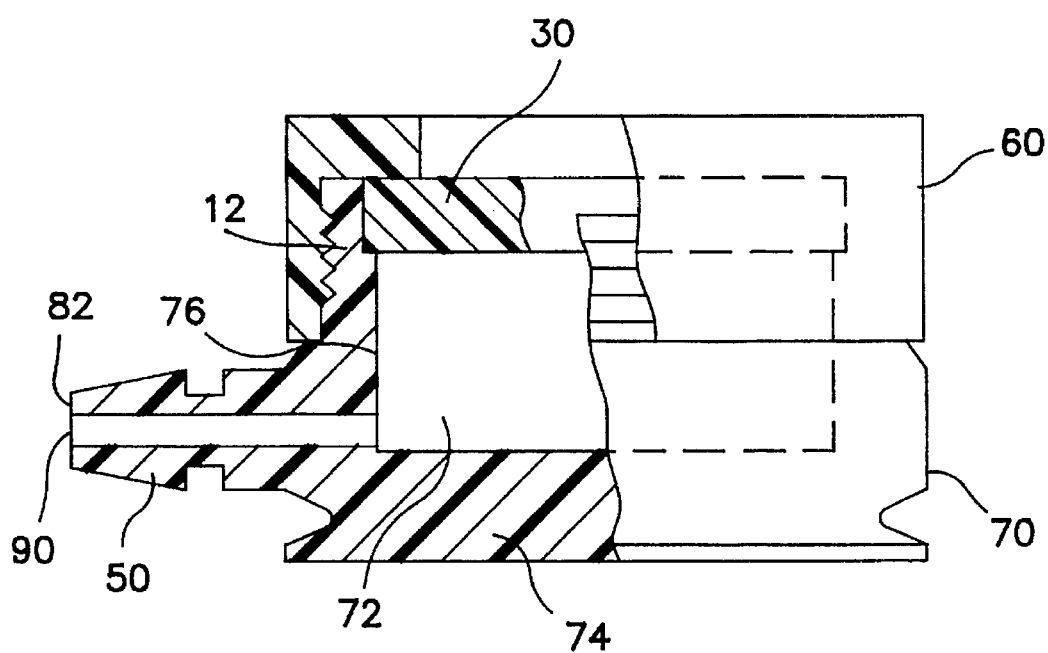
FIG. 2 is an enlarged side view, cut away, of the subcutaneous infusion port of the present invention showing aspects of its internal construction.

As shown in FIG. 2, the housing 70 has side wall 76 and a bottom wall 74. The space between the diaphragm 30 side walls 76 and the bottom wall 74 defines an inner chamber 72 having a volume for receiving a fluid to be introduced or withdrawn from a patient's body following implantation of the infusion port. The volume of the chamber can vary depending upon the contemplated end use for the infusion site. In the embodiment shown in FIG. 2, the chamber sidewall 76 is generally a straight, vertically extending sidewall and extends in a circle, forming a generally cylindrical chamber 72. The chamber 72 can have geometric configurations other than cylindrical such as a generally frustoconical portion narrower near the entry port.

Figure 4:
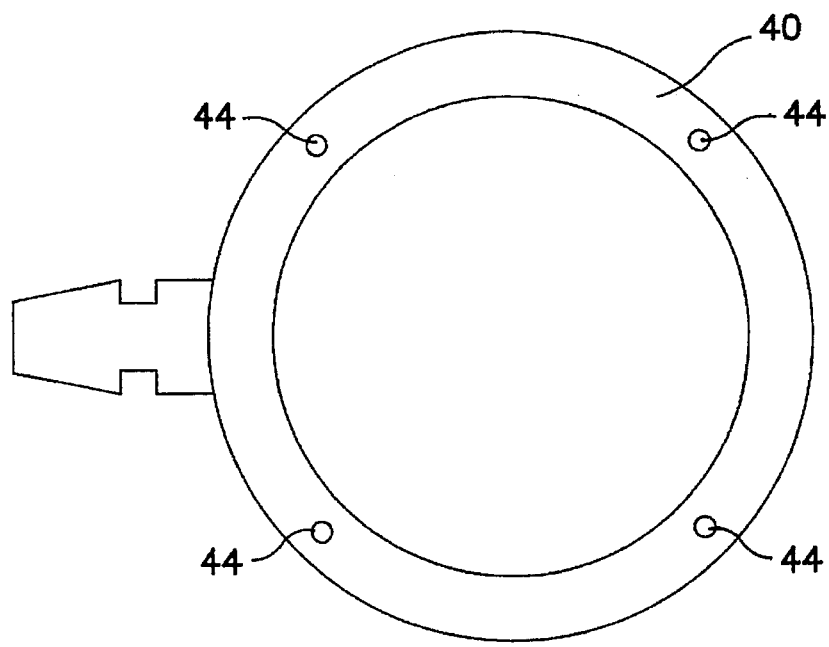
FIG. 4 is a top elevational view of the present invention.

The housing 70 has an attaching means to provide attachment of the housing 70 to a location within the patient. In a preferred embodiment, the housing 70 can include a radially extending flange 40. As can be seen in the drawings and especially in FIG. 4, the outwardly extending flange 40 extends around the periphery of the infusion port. In another embodiment, the flange can extend around only portions of the periphery of the injection site. One purpose of the flange is to provide for attachment of the infusion port to a location within a patient. For example, the flange may include suture sites 44 through which sutures can be taken to fix the infusion port subcutaneously within a patient. Other techniques for fixing the infusion port within the patient can be used such as using surgical staples. The suture sites 44 can be apertures opening through the outwardly extending flange or can merely be areas along the flange of lesser thickness or can merely be areas along the flange of lesser thickness than the flange itself such that such suture sites can be easily penetrated by a surgical needle with suturing.

In a preferred embodiment, a conduit 50 extends from the housing 70 in alignment with the fluid transfer opening 90. The conduit 50 can be integrally molded with the housing 70 to avoid any connection seams which are a possible source of leakage. A conduit 50 communicates with a fluid receiving site in the body such as a catheter. The outside diameter of the conduit 50 is designed to firmly anchor the distal end of the catheter to the conduit 50. Such methods of firmly anchoring the catheter to the conduit 50 include a plurality of barbs on the outer diameter of the conduit 50 to "pushpull" lock onto the catheter; a snaplock connector on the catheter that mates with the conduit 50; and an O-ring disposed on the conduit 50 that fits over the catheter to firmly anchor the catheter to the housing 70. In another embodiment, the conduit 50 can have a sleeve that fits over the catheter to protect the catheter from possible needle punctures.

Figure 3:
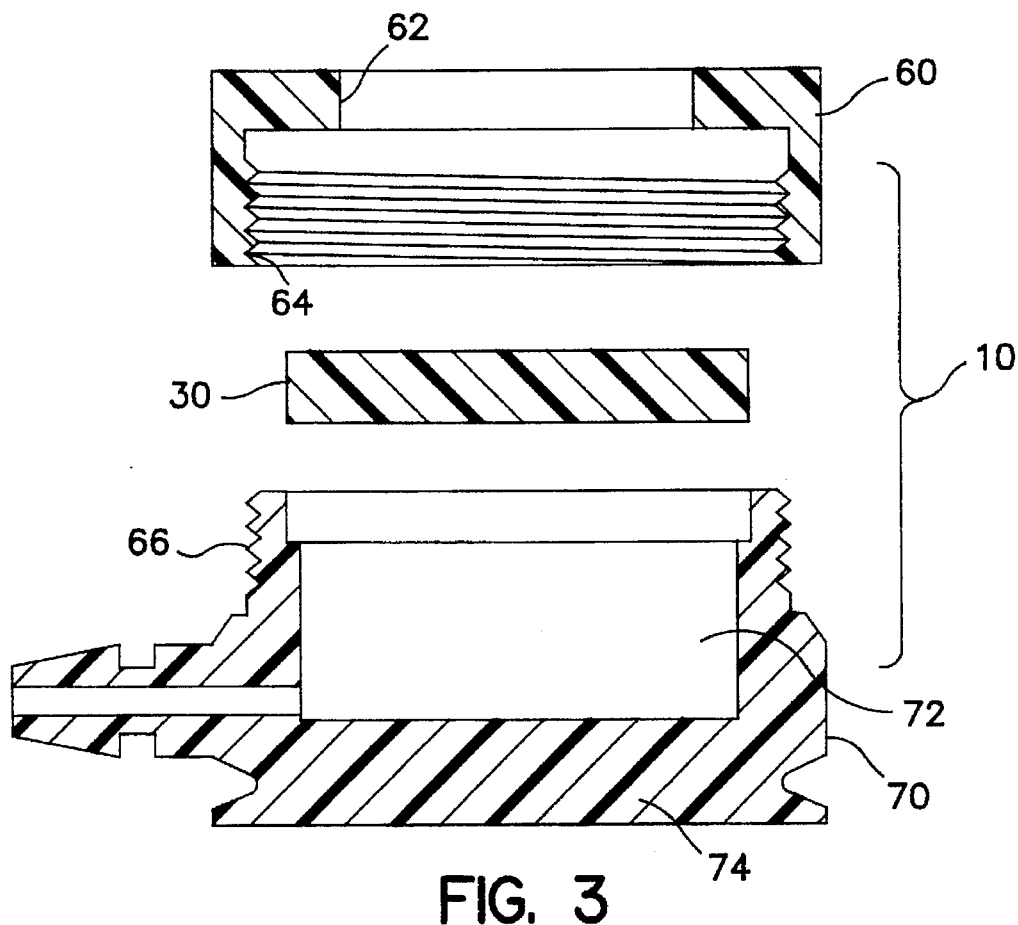
FIG. 3 shows the screw arrangement of the present invention with the pieces in separate condition.

Referring now to FIG. 3, the subcutaneous infusion port 10 separates into three pieces: (1) a housing 70; and (2) a diaphragm 30; and (3) a sealing means 60 to securely fasten the diaphragm 30 to the housing 70 and to provide a leak resistant seal between the diaphragm and housing. This design allows for ease of replacement of the diaphragm. In addition, the present invention allows for replacing either or all parts individually. Thus, the housing 70 with the connection to the catheter or, if necessary, the diaphragm 30 can remain in place. The procedure for replacing the diaphragm is simple and could take place on an out-patient basis. Under local anesthesia, an incision is made in the skin near the infusion port 10. In a preferred embodiment, then, the diaphragm 30 is sharply dissected free and the sealing means 60 is twisted off. Subsequently, the diaphragm is removed and a new diaphragm 30 is inserted. Finally, the sealing means 60 is twisted tightly back on housing 70 and the wound is closed with sutures.

The dimensional relationship between the sealing means 60 and the diaphragm 30 is selected such that the seating of the sealing means 60 on the diaphragm 30 in the side wall causes a leak resistant seal. The sealing means 60 is threaded to an outer side wall 66 to provide the desired sealing force between the diaphragm 30 and the housing 70.

In another embodiment, the sealing means 60 may be modified to employ another type of means for sealing the diaphragm 30 to housing 70. For example, the sealing means 60 may be modified to be a clamp ring having projections that are then aligned with slots on the top of housing 70 to permit entry of the projection attached to sealing means 60. The sealing means 60 is then rotated to move the projections past the slots to lock the sealing means 60 into housing 70. The sealing means 60 thus squeezes the diaphragm against the housing 70 to provide a leak-resistant seal between the sealing means 60 and the housing 70 and to securely hold the diaphragm 30 to the housing 70.

In another embodiment, the subcutaneous infusion port of the present invention may have more than three pieces but the design is such that the diaphragm 30 is easily removed from the housing 70.

The precise dimensions of the subcutaneous infusion port 10 may vary since they are based upon both the application and the implant location. For example, in peritoneal dialysis, the infusion port of the present invention should be sized for: (1) high flow rates (above 100 ml/min); (2) low flow resistance; (3) large needles; and (4) optimal surface area in both thickness and diameter of the diaphragm for sufficient tissue in-growth and allowing for repeated needle puncture. Thus, fluid transfer opening 90 of the conduit 50 must be sufficiently sized to allow for large flow rates and low resistance. In addition, the inner chamber 72 must be sufficiently sized to allow for large flow rates. Thus, since the infusion port 10 must be of sufficient size, the diaphragm 30 must also be sufficiently sized to allow for peritoneal dialysis.

In an embodiment that may be suitable for the peritoneal dialysis, the housing 70 can have an outer diameter of approximately 3 centimeters. The diaphragm can have a thickness of approximately 5-10 millimeters and an outer diameter of approximately 2.6-2.8 cm. An inside diameter 62 of the screw ring 60 can be approximately 2.6 cm. and the outside diameter 64 can be approximately 3-4 cm. The inner chamber 72 can have a diameter of approximately 2.7 cm. The conduit 50 can have an inner diameter for the fluid transfer opening 90 of approximately 3.4 mm and an outer tapered diameter of approximately 4-5 mm. The height of the port 10 can be approximately 2-2.5 cm. The wall thickness of the housing 70 can be approximately 1-2 mm.

The size of the present invention can be modified according to the requirements for the treatment technique to which the infusion port is being used. That is, the size can be varied to provide for palpation, different needle sizes, number of injections and expected back pressures in order to accomplish the desired resealing characteristics. In this manner, the infusion port can be modified to meet the demands for placement of the connecting catheter into different body structures such as intrathecal intravenous, intraarterial and intraperitoneal areas.

Specific examples illustrating the subcutaneous infusion port of the present invention are set forth below without necessarily limiting the scope of the invention.

EXAMPLE 1

The following test was designed to determine the ex-vivo gravity drainage rate through the subcutaneous infusion port of the present invention in comparison to the standard transcutaneous Tenckhoff type peritoneal catheter method for acute renal failure.

The subcutaneous infusion port employed the following design: (a) outer diameter of housing 2.5 cm.; (b) diaphragm thickness of 0.5 cm. and outer diameter of 2.2 cm.; (c) the diaphragm was composed of a composite of silicone elastomer and fabric; (d) diameter of inner chamber of 1.8 cm.; (e) inner diameter of conduit of 3 mm; (f) height of port of 2 cm.; and (g) the port was composed of plastic.

Ex-vivo gravity drainage rate through the present invention connected to the Tenckhoff catheter and accessed with a 15 gauge needle ("SIP-needle-catheter") was determined from a fixed height of 30 inches. The SIP-needle catheter system had a mean flow rate of 133+/−2.4 ml/min compared with a standard Tenckhoff peritoneal dialysis catheter which had a mean flow rate of 425+/−8.8 ml/min ($p<0.001$) [where p is significant value].

EXAMPLE 2

The following test was designed to determine the effectiveness of the subcutaneous infusion port of the present invention in comparison to the standard transcutaneous Tenckhoff dialysis catheter method for acute renal failure. The subcutaneous infusion port described in Example 1 was employed. Twenty New Zealand white rabbits (1.5 to 3 kg)

underwent bilateral nephrectomy. Group ND (N=4) had no dialysis catheter implanted. Group SIP (n=8) had the subcutaneous infusion port of the present invention with dialysis catheter implanted. Group TKH (n=8) had a conventional transcutaneous Tenckhoff dialysis catheter implanted. Blood urea nitrogen (BUN) and serum creatinine samples were collected pre-operatively for all groups and then daily for groups ND, and pre- and post- dialysis for groups SIP and TKH on each day of the study. On post-operative days 1–4, animals in groups SIP and TKH underwent peritoneal dialysis with 100 ml per kg of 2.5% Dianeal solution for four 30-minute dwell periods.

For group SIP, dialysis on day four resulted in a mean BUN and serum creatinine of 73+/–4 mg/dl and 8.2+/–0.4 mg/dl respectively and for group TKH 84+/–4 mg/dl and 10.0+/–mg/dl, respectively. Both methods resulted in a significant reduction compared to group ND which had a mean BUN of 197+/–10 mg/dl and mean serum creatinine of 14.9+/–1.5 mg/dl (p<0.05).

The mean post-dialysis percent decrease in BUN and serum creatinine for group SIP was 30+/–3% and 21+/–1%, respectively. This was not significantly different from the mean post-dialysis percent decrease for group TKH of 28+/–3% and 18 +/–2% for BUN and serum creatinine, respectively.

The results of the above data in Example 2 showed no significant difference in the decrease in BUN or serum creatinine among groups undergoing dialysis by the method employing the present invention or the method employing the traditional transcutaneous catheter. Therefore, although the present invention had slower flow rates than the traditional transcutaneous catheter, equally effective dialysis was accomplished. Thus, the present invention is capable of replacing the conventional transcutaneous catheter for peritoneal dialysis.

EXAMPLE 3

The following test is designed to determine the ability of the present invention compared to a conventional subcutaneous infusion port to reseal after repeated needle punctures with a large needle (15 gauge) that is employed in peritoneal dialysis.

Thirty (30) male New Zealand White rabbits undergo implantation of two subcutaneous infusion ports ("SIP") dialysis devices. The two SIP devices are implanted between the shoulder girdles of each rabbit. One device is an SIP composed of a conventional silicone elastomer diaphragm and the other device is an SIP of the present invention composed of the composite diaphragm. Each device is connected to a dialysis catheter and the catheter is tunneled subcutaneously and inserted into the peritoneum through a small incision.

Animals are allowed to recover for two weeks. Afterwards, the diaphragm of both SIP devices are punctured with a 15 gauge, non-coring needle, and the catheter is flushed with 10 ml of normal saline.

Animals undergo daily weekday punctures of each SIP device for two weeks and are then sacrificed at the third day after the last puncture. The SIP devices are then removed and the leak pressures determined in a pressure measuring chamber discussed below. The SIP is removed in continuity with the skin. The skin and subcutaneous tissue are dissected free from fibrous tissue in-growth of the diaphragm.

The pressure measuring chamber has been constructed to measure the pressure within the device at which the diaphragm of each SIP begins to leak. The SIP is placed in the pressure measuring chamber (PMC) and continuous pressure is applied to the SIP during methylene blue saline installation at a constant flow rate through the SIP catheter conduit. Pressure measured at the first sign of egress of methylene blue determines the leak pressure (LP).

The results show that the SIP device of the present invention withstands a higher pressure prior to showing any leakage when compared to the SIP device with the conventional silicon elastomer diaphragm. This is a direct result of the novel composite diaphragm of the present invention comprising a top layer of collagen which results from tissue in-growth.

What is claimed:

1. A subcutaneous infusion port for peritoneal dialysis, comprising:

(a) a housing forming an inner chamber and including (i) a vertically extending side wall disposed about the chamber, the side wall having a first and a second axially spaced ends and inside and outside side walls, the side wall forming a generally cylindrical chamber;

(ii) an entry port into the chamber located at the second end of the side wall;

(iii) a bottom solid wall axially disposed at the first end of the side wall;

(iv) an attaching means disposed at the first end of the side wall for fixing the housing to a patient;

(b) a replaceable self-sealing, self-healing, needle penetrable diaphragm axially located near the second end of the sidewall for sealing the entry port and for maintaining the sealed inner chamber, the diaphragm comprising:

(i) a bottom layer constructed of a material having properties of being inert, impermeable to fluid and preventing tissue in-growth and the bottom layer facing the bottom solid wall;

(ii) a layer above the bottom layer and laminated to the bottom layer, the layer above the bottom layer constructed of a material having properties that promote tissue in-growth;

(c) a removable sealing means in contact with both the side wall and the diaphragm in order to securely hold the diaphragm to the housing and to provide a leak resistant seal between the diaphragm and housing;

(d) a conduit for attaching to a standard dialysis catheter, wherein said conduit extends out from the outside side wall and is located near the first end of the side wall, the conduit having a fluid entry port which is in alignment with the conduit and which interconnects with the inner chamber for a fluid flow passage.

2. A subcutaneous infusion port according to claim 1, wherein the bottom layer of the diaphragm is composed of a layer selected from the PTFE group consisting of polytetrafluoroethylene and expanded porous polytetrafluoroethylene and a uniform layer of an elastomer glue located directly above the PTFE layer.

3. A subcutaneous infusion port according to claim 1, wherein the layer above the bottom layer and laminated to the bottom layer of the diaphragm is selected from the group consisting of dacron, nylon, cotton, polyethylene and polypropylene.

4. A subcutaneous infusion port according to claim 1, wherein the attaching means includes a radially extending flange that extends around the periphery of the infusion port, the flange having one or more suture sites to fix the infusion port to a patient.

5. A subcutaneous infusion port according to claim 1, wherein the sealing means includes a screw ring that twists off the housing for diaphragm replacement.

6. A subcutaneous infusion port according to claim 1, wherein the conduit attaches to a standard dialysis catheter.

7. A subcutaneous infusion port according to claim 1, wherein the bottom wall is composed of a material that is virtually impenetrable by a hydrodermic needle.

8. A subcutaneous infusion port according to claim 1, wherein the housing is selected from the group consisting of polyethylene, polycarbonates, polyurethane, polyvinyl chloride, and metals such as stainless steel and titanium.

9. A subcutaneous infusion port according to claim 1, wherein the removable sealing means is designed to allow for ease of replacement of the diaphragm without having to remove the housing.

\* \* \* \* \*